(12) United States Patent
Schnabel

(10) Patent No.: US 6,433,247 B1
(45) Date of Patent: Aug. 13, 2002

(54) **BALLISTIC TRANSFORMATION OF *C. ELEGANS***

(75) Inventor: Ralph Schnabel, Braunschweig (DE)

(73) Assignee: Devgen N.V. (BE)

( * ) Notice: Subject to any disclaimer, the term of this patent is extended or adjusted under 35 U.S.C. 154(b) by 0 days.

(21) Appl. No.: 09/273,965

(22) Filed: Mar. 22, 1999

(30) Foreign Application Priority Data

Mar. 23, 1998 (GB) .............................................. 9806211
Sep. 11, 1998 (GB) .............................................. 9819868

(51) Int. Cl.$^7$ ........................ C12N 15/00; C12N 15/63; C07H 21/02; C07H 21/04
(52) U.S. Cl. ...................... 800/21; 536/23.1; 536/23.5; 435/455
(58) Field of Search ................................ 800/8, 13, 21; 536/23.1, 23.5; 435/455

(56) References Cited

U.S. PATENT DOCUMENTS 5,120,657 A     6/1992    Agracetus ................ 435/285.3

FOREIGN PATENT DOCUMENTS

WO     WO 93/24626     12/1993

OTHER PUBLICATIONS

Mello et al., EMBO Journal, 10(12), pp. 3959–3970, Dec. 1991.*
Villee et al., General Zoology, 6th Edition, Saunders College Publishing, pp. 509, 1984.*
Palmiter et al., Science, vol. 222, pp. 809–814, 1983.*
Pursel et al., J. Reprod. Fert., Suppl. 40, pp. 235–245, 1990.*
Kappel et al., Current Opinion in Biotechnology, 3: 548–553, 1992.*
Christou, Paul, Methods in Cell Biology, vol. 50, pp. 375–382, 1995.*
Wittmann et al., Development, vol. 124, pp. 4193–4200, 1997.*
Zelenin et al., FEBS Letter, vol. 287 (1,2), pp. 118–120, 1991.*
Granato et al., Nucleic acids Research, vol. 22 (9), pp. 1762–1763, 1994.*
Rushforth A. et al., "Transformation of *C. Elegans* by DNA Coated Microprojectiles," Abstract No. 223 at 1989 International Worm Meeting.
Harrington, T. et al., "DNA Transformation Using Electrically Charged Tungsten Microelectrodes," *Proc. South. Biomed. Eng. Conf.*, 14th, pp. 12–15 Publisher: Institute of Electrical and Electronics Engineers, New York, NY (1995).
Hashmi S., et al., "GFP: Green Fluorescent Protein a Versatile Gene Marker for Entomopathogenic Nematodes," *Fundam. App. Nematol.*, 20(4):323–327 (1997).
Mello, C., et al., Efficient Gene Transfer in *C. Elegans*: Extrachromosomal Maintenance and Integration of Transforming Sequences, *The EMBO Journal*, 10(12):3959–3970 (1991).
Wilm, T., et al., "Ballistic Transformation of *Caenorhabditis Elegans*,"*Gene*, 229:31–35 (1999).
*Methods in Molecular Biology* (1997), 62.393–398—Sarwar Hashmi, et al., Application of Piercing Structures for Genetic Transformation of Nematodes.
*Genetic Engineering* (1996), 18.135–155—Randy Gaugler, et al., "Genetic Engineering of an Insect Parasite"—especially p. 140, line 25 to p. 141, line 11.
*J. Invertebrate Pathology* (1995), 66.293–296—Sarwar Hashmi, et al., "Genetic Transformation of an Entomopathogenic Nematode by Microinjection".
*Bio/Technology* (1992), 10.286–291—Theodor M. Klein, et al., "Transformation of Microbes, Plants and Animals by Particle Bombardment".

* cited by examiner

*Primary Examiner*—Scott D. Priebe
*Assistant Examiner*—Shin-Lin Chen
(74) *Attorney, Agent, or Firm*—Wolf, Greenfield & Sacks PC

(57) ABSTRACT

A ballistic method of introducing nucleic acid into a nematode worm is described which involves bombarding the nematode with a plurality of microprojectiles. Nematode worms transformed according to the method of the invention are also provided.

17 Claims, 1 Drawing Sheet

BALLISTIC TRANSFORMATION OF C. ELEGANS

Figure 1:

The invention is concerned with a method of introducing nucleic acid into nematode worms, in particular *Caenorhabditis elegans*.

Transgenic *Caenorhabditis elegans* (*C. elegans*) are currently made by injecting nucleic acid (usually DNA) into the hermaphrodite gonad (i.e. into a syncitium) or into individual oocyte nuclei. Typically one injects a mixture of the DNA one wants to introduce (hereinafter referred to as 'test DNA') and a plasmid carrying a selectable marker that allows one to distinguish transgenic progeny from non-transgenic progeny. The selectable marker can be a visible phenotypic marker which leads to a change in shape or movement of the transgenic worms (e.g. rol-6), a marker rescuing a conditionally lethal gene introduced into the genetic background of the injected worms or a plasmid containing nucleic acid encoding green fluorescent protein (GFP) from the jellyfish *Aequorea victoria*. The offspring of injected worms (F1 generation) are then screened for animals expressing the selectable marker.

The F1 offspring of an injected hermaphrodite typically contain on average 1 to 10 individuals that express the selectable marker. These individuals are then placed in culture but on average only 10% will go on to transmit the selectable marker to their offspring. One generally assumes that when the marker DNA is accepted into the worm genome and transmitted to the offspring, the test DNA which one wants to introduce is co-transformed.

This current method of transformation has practical limitations in that introducing DNA into worms entails one by one manipulation and injection of syncitia/oocytes under a microscope. This work is time consuming and requires a considerable amount of expertise. It is typically possible for a person skilled in the injection technique to inject ~50 hermaphrodites in a single day.

Transgenic worms transmitting the transformed DNA in a heritable manner have incorporated an extra minichromosome, consisting of a mixture of marker and test DNA linked together in an unpredictable structure. This minichromosome is mitotically and meiotically unstable and is lost at a rate of 1% to 99% per cell division.

It is an object of the present invention to provide a more efficient transformation system for *C. elegans*. Ideally one would wish to achieve integration of the exogenous test DNA by homologous recombination with the *C. elegans* chromosome. In order to achieve this aim it will be necessary to develop a technique by which DNA can be simultaneously introduced into a large number i.e. thousands of individual worms.

A recently developed method for introducing DNA into cells involves shooting cells with microprojectiles, typically gold or tungsten particles of around 2 µm diameter, which have been coated with the DNA to be introduced. This technique, generally known to persons skilled in the art as ballistic transformation, has been used to successfully deliver DNA into plant cells (Klein et al. Nature, 327: 70–73 (1987); Christou et al. Plant Physiol., 87: 671–674 (1988); Takeuchi et al. Plant Molecular Biology, 18: 835–839 (1992)), cultured mammalian cells (Zelenin et al. FEBS Letters, 244: 65–67 (1989)), fertilized fish eggs (Zelenin et al. FEBS Letters, 287: 118–120 (1991)) and intact mouse tissues and organs (Zelenin et al. FEBS Letters, 280: 94–94 (1991); Williams et al. Proc. Natl. Acad. Sci. USA, 88: 2726–2730 (1991)).

Despite the success of the technique with plant cells and cultured mammalian cells problems have been anticipated by those skilled in the art in applying ballistic techniques to nematode worms. However, the present inventors have successfully applied a similar ballistic transformation technique to the introduction of nucleic acid into *C. elegans*. Using this technique it is possible to introduce nucleic acid simultaneously into a large number of individual worms.

Accordingly, in a first aspect the invention provides a method of introducing nucleic acid (DNA and/or RNA) into a nematode worm comprising bombarding the worm with a plurality of microprojectiles.

In one embodiment of the invention the microprojectiles are coated with the nucleic acid which it is desired to introduce into the nematode worm.

Bombardment of the nematode worm with high velocity microprojectiles is achieved using a particle bombardment gun based on flowing helium of a type known in the art, see for example Johnston, Nature, 346: pp776; Klein et al. Biotechnology, 10: pp286–291 and Takeuchi et al. Plant Mol. Biol., 18: pp835–839. The gun uses a flowing stream of helium gas to accelerate DNA coated particles towards a target sample to be transformed.

A detailed protocol for ballistic transformation of *C. elegans* using nucleic acid coated microprojectiles is described in the examples given herein. Briefly, a small pellet of worms is dispensed onto a small nematode agar plate. The plate is then placed inside the 'gun' and a suspension of microprojectiles (e.g. gold particles) coated with nucleic acid is shot at the worms. After a short recovery period the plate is cut into a number of segments which are placed on large agar plates to grow worms for selection of transgenic animals. The transformation procedure takes only a few minutes and is technically very simple so that a large number of experiments can be undertaken in very little time.

In an alternative embodiment of the method of the invention ballistic transformation can also be accomplished by first applying a solution containing the nucleic acid directly onto the nematodes and then shooting the nematodes with 'bare' microprojectiles which have not been coated with nucleic acid. With this technique it is not necessary to coat the microprojectiles with nucleic acid. Using the conventional bombardment technique (i.e. using coated microprojectiles) transformed offspring are produced as a result of a coated particle being fired into a gonad cell of the worm. Using the alternative approach, in which the worms are first coated with a dense solution of nucleic acid and then bombarded with 'bare' microprojectiles, a particle may drag the DNA along its passage through the worm and hence the particle does not necessarily need to stop within a gonad cell. If the particle merely passes through a gonad cell on its passage through the worm it may leave behind a sufficient amount of the nucleic acid it is dragging along to result in transformation of the gonad cell.

In order to facilitate selection of transformants into which DNA has been successfully introduced by the method of the invention it is preferred to use a dual selection protocol using a dominant phenotypic marker such as, for example, rol-6 or an autonomous fluorescent protein (AFP) in combination with a marker rescuing a conditionally lethal gene introduced into the genetic background of the injected worms. As used herein the term "autonomous fluorescent protein" encompasses both green fluorescent protein (GFP) and blue fluorescent protein (BFP) and any other autonomous fluorescent protein of this type. The examples given below relate to the transformation of *C. elegans* with a genetic background carrying a temperature sensitive mutation in the pha-1 gene wherein DNA encoding the wild-type pha-1 gene is introduced as a co-selectable marker. However, other conditional lethal mutations could have been used with equivalent effect and it is to be understood that the present invention is not to be limited by the nature of the selectable markers employed to facilitate the identification of transformed worms.

The present invention will be further understood with reference to the following Examples, together with the accompanying Figure.

FIG. 1 shows a Normarski micrograph of *C. elegans* which have been bombarded with gold particles. The upper arrow points at a gold particle located in the gonad, the lower arrow on one located in the intestine of a young hermaphrodite.

EXAMPLE 1

Basic Protocol for Ballistic Transformation (A) Synchronised Worm Culture

1. *C.elegans* worms (strain pha-1(e2123ts)) were grown on large standard NGM-plates to starvation to promote accumulation of larvae of the L1 stage.
2. Pieces of agar containing 'L1-islands' were cut out and used to inoculate fresh large NGM-plates.
3. The worms were grown up to the young adult stage at 15–20° C. depending on the requirements of the particular *C. elegans* strain in clean pseudo-sterile surroundings.
4. Worms were washed off the plates with distilled water or egg-buffer, pooled in 50 ml Falcon tubes and allowed to sediment by gravity.
5. Approximately 500–800 µl aliquots of the worm pellet were aspirated using a Gilson® pipette equipped with a blue tip and placed dropwise in the centre of small NGM-plates.
6. The plates were placed on ice and the liquid allowed to soak in leaving back a heterogenous worm "pillow". The worm pillow was formed into a circular shape of approximately 10 mm diameter using a platinum spatula and left on ice until use.

(B) Ballistic Particle Bombardment

1. An NGM plate containing the ice-cooled worms was placed on the crosshair table within the vacuum chamber of the gun, with a distance of 120 mm to the opening of the shooting chamber. The lid of the NGM plate was removed and the door of the vacuum chamber immediately closed. The steel grid within the shooting chamber was then loaded with DNA-coated gold suspension (in ethanol). The gold particles were coated with a mixture of test DNA and marker DNA (plasmids pRF4 containing rol-6 and pBX containing wild-type pha-1).
2. The helium pressure presetting valve was set to 8–10 bar. The vacuum chamber was then evacuated, the pressure discharge being released when the partial vacuum reached a pressure of −50 to −100 mbar.
3. The door of the vacuum chamber was then opened and the lid of the NGM plate immediately replaced to preserve sterility. The plate was then placed at 15° C. to allow the worms to recover from the bombardment procedure.
4. The NGM agar was cut into 4–8 segments and each segment placed on a fresh large enriched NGM plate (double tryptone). The large plates were then incubated at 15–20° C.

(C) Selection for Transformants

After 6 to 7 days post-transformation the F1 worms were screened:

(i) visually for worms expressing the rol-6 phenotype, those expressing the rol-6 phenotype being isolated and subsequently tested for stable transformation, and/or
(ii) by shifting to 25° C. and maintaining in culture for a further 3 to 4 days to screen for pha-1 rescue, and/or following either of the above
(iii) individual transgenic worm lines both expressing the rol-6 phenotype and exhibiting pha-1 rescue at 25° C. were then individually tested for the presence of the test DNA using techniques known in the art.

EXAMPLE 2

Detailed Protocol for Ballistic Transformation

The methods used are described in the form of a recipe. All steps are carried out under sterile conditions. General *C. elegans* methods are described in Wood W. B. (1988) 'The nematode *Caenorhabditis elegans*', Cold Spring Harbor Laboratory, New York.

(A) Preparation of Worms

Grow target worm strain (here pha-1 (e2123ts)) on large standard NGM-plates (90 mm diameter) to starvation so that plates are covered with many islands of L1 larvae. Depending on the size of the 'L1-islands' cut out agar pieces of 5–10 mm$^2$ and inoculate about 8 fresh large NGM plates per 10 shots. Worms should not starve before they reach adulthood. The worms can be fed on bacteria such as *E. coli*. Plates are ready when about 50% of the worms contain a few eggs. Wash the worms off the plates with distilled water and pool in 50 ml tubes. Let the worms sediment down by gravity (~15 min at room temperature). Approximately 100 µl of the worm pellet are placed in the centre of small (35 mm) NGM-plates. These plates have been dried for several days and are seeded the day before (incubation at RT) with a thin layer of *E. coli* (strain OP50) with diameter of approximately 10 mm. Put the plates back on ice to stop the worms from moving about and let the liquid soak up leaving back a heterogeneous worm "pillow". Take a platinum spatula and form a more or less homogeneous and circular shaped worm "pillow" with a diameter of about 10 mm. Leave on ice until use; not longer than 1–2hrs.

(B) Ballistic Particle Bombardment

The bombardment device (gun) is calibrated by shots at a filter paper placed at shooting distance (see below) and subsequent drawing of a crosshair through the centre of the target area. Calibration should be repeated from time to time. Set the He pressure pre-setting valve to 8–10 bar for calibration and transformation. Place and adjust the ice-cooled worm plate on the crosshair table within the gun vacuum chamber with a distance of 120 mm to the filter holder, take off the plate's lid only before closing the chamber. Load the steel grid within the shooting chamber with the DNA-coated gold suspension in EtOH. Start to evacuate the vacuum chamber and trigger the gun (pulse time approximately 10 ms; the pressure wave should not release the lid of the device for pressure release) when the partial vacuum reaches values of 50 to 100 mbar.

We were not able to determine settings which gave significantly the best result for either the bombardment pressure or the partial vacuum. A systematic analysis of this might be useful for an individual apparatus. Worms survived even stronger partial vacuum and might also be transformable with less then 8 bar pressure.

Release the vacuum and immediately close the worm plate again. Allow the worms to recover at 15° C. for approximately 30 minutes. Worms will warm up and start moving again. Cut the agar into 4 or more sectors and put each piece on a fresh 90 mm enriched NGM-plate (double tryptone). Leave plates at 15–20° C. depending on the selection protocol for trangenes.

(C) Screening Procedure

This procedure may vary depending on the actual system used to screen for transgenic worms. In case of using rol-6 (Mello, C. C. et al. (1991) EMBO J. 10: 3959–3970) and /or pha-1 (Granato, M. et al. (1994) Nucl. Acids Res. 22: 1762–1763):

Search for rol-6 animals among the F1 generation after 6–7 days (15° C.). Rol animals are placed on individual plates and subsequently tested for stable transformation. Stable transgenic lines should produce rol-6 offspring in a non-Mendelian ratio. The remaining F1 generation is shifted to 25° C. and tested for pha-1 rescue after another 3–4 days. Rescue is indicated by the appearance of young F2 larvae on the plates. Check plates again after another 3–4 days. If viable worms are found, 10–20 of these F2 or F3 animals are individually tested for stable transformation by non-Mendelian segregation of dead eggs and viable worms. It should be noted that pha-1 reverts occasionally by acquiring spontaneous second site suppressors (Schnabel, H. et al. (1991) Genetics, 129: 69–77). Therefore the pha-1 strain should be checked regularly for its integrity by shifting some worms to 25° C., where pha-1 produces only dead eggs. The presence of the ceh-13 GFP reporter construct was tested directly by viewing embryos from transgenic hermaphrodites under a fluorescence microscope. To test for rescue of the non-conditional allele t1237 of the maternal effect embryonic lethal gene sud-1 the transgenic array was crossed into a sud-1 background (vab-9 sud-1 (t1237)/mncl; lon-2) and the progeny of homozygous Vab hermaphrodites (vab-9 sud-1) was screened for viability.

(D) Preparation of Gold Particles for Ballistic Bombardment

The recipe is based on the method of Takeuchi et al. (1992) Plant Mol. Biol., 18: 835–839. 5 mg gold powder (Au; powder, spherical, Ø 1.5–3 µm; Aldrich®) is placed in an 1.5 ml Eppendorf tube and the particles are prewashed with 500 µl distilled water; a homogeneous suspension should appear after vortexing. Let the gold particles sediment and discard the water carefully. Add a small volume of fresh distilled water and 20 µg of each plasmid DNA. Adjust volume to 180 µl with water and add 20 µl of a 3M Na-acetate solution. Vortex. The DNA is precipitated with 2.5 volumes EtOH. Store for 30 min at −20° C. Vortex several times during this period. Settle the Gold particles by gravity and aspirate the supernatant. Do not centrifuge. Suspend the particles in 200 µl ice-cold absolute EtOH. Vortex. Particles can now be stored at −20° C. For transformation load 20 µl (approximately 2–6 µg of DNA per shot) of the suspended solution in the filter paper of the Swinny®-Filterholder (Millipore) used for bombardment. Mount and shoot immediately.

An alternative method for preparing the Gold particles is as follows:

Add 20 µg of plasmid DNA to 10 mg Gold powder (Au; powder, spherical, Ø 1.5–3 µm; Aldrich®). Add distilled water to a total volume of 200 µl then add 20 µl 3M Na-acetate and 550 µl ethanol and place at −20° C. for at least three hours, with vigorous vortexing every 30 minutes, to precipitate the DNA. After 3 hours let the Gold particles sediment, aspirate the supernatant and re-dissolve the Gold particles in 200 µl ice-cold ethanol. 20 µl of this solution is used for each experiment.

(E) Preparation of Glass Particles for Ballistic Bombardment

As an alternative to Gold particles ballistic transformation may also be performed with glass microprojectiles prepared as follows:

Add 20 µg plasmid DNA to 10 µl of 'glassmilk' activated glass suspension (Jetsorb) and add 300 µl buffer A1 (supplied with the glassmilk suspension by the manufacturer). Allow the DNA to bind to the glassmilk for 15 minutes at 53° and after centrifugation wash the pellet with 300 µl buffer A1. The resultant suspension is re-pelleted by centrifugation then washed twice with buffer A2 (also supplied by the manufacturer with the glassmilk suspension). After washing the pellet is dried and re-suspended in 200 µl of ethanol. 20 µl aliquots are used for each transformation experiment, following the ballistic bombardment procedure as described above for Gold particles. Other activated glass suspensions from other manufacturers can also be used in this procedure.

Although activated glass suspensions are known to bind DNA, probably even better than gold, ballistic transformation experiments with glass particles did not result in enhanced transformation efficiencies. Although probably more DNA is bound to the beads, glass has a lower density than gold and will probably be less efficient to penetrate the nematode. Nevertheless, it is possible to transform *C. elegans* with glass particles at approximately the same efficiencies as with gold particles, indicating that neither the quantity of introduced DNA nor the density of the particle is of major importance.

Results

The results of a number of independent ballistic transformation experiments using Gold particles, performed according to the protocols described above, are summarised below. In each case the nature of the test DNA and marker DNA is given. For each test DNA/marker combination a number of different bombardment procedures were performed according to the method given in part (B) above. Transformants were then scored for expression of rol-6 phenotype and rescue of the pha-1 conditional lethal mutation.

In general, using rol-6 selection an average of two transformants per shot was obtained by scoring the F1 for rolling animals on the large plates derived from each shot (step 4 of part (B)). As with the microinjection protocol only 10% of these were stable during the next generations (one line in 6 shots). These lines always also expressed two other co-transformed plasmids (pha-1 in conjunction with either a GFP-reporter construct of ceh-13 (Wittmann, C. et al. (1997) Development, 124: pp4193–4200) or a plasmid containing the sud-1 gene, see the results summarised in Table 10A. Using the pha-1 selection system approximately one stable line per two shots was obtained by shifting the plates to the non-permissive temperature for rescue in the F2 generation. The pha-1 selection system is thus three times more effective than the rol-6 system in selecting transformed animals. The pha-1 transgenic animals also co-expressed a second marker, however, co-transformation occurred with a slightly lower frequency (70%) than in the animals from the same shots selected for stable rolling after the first generation (Table 10B). It is possible that the co-transformation depends initially on a critical amount of DNA so that the different DNAs are reliably co-ligated to form concatemeric arrays (Mello, C. C. et al. (1991) EMBO J., 10: pp3959–3970). By selecting with the less sensitive rol-6 phenotype one may just miss animals below a certain threshold and thus select for animals which had a higher chance for co-ligation.

Table 11 shows a detailed analysis of a series of shots. A certain clustering of the transformation events was observed. Nine out of the fourteen plates with lines transformed for pha-1 in the F2 selection carried Rol animals in the F1 selection. Also, stable lines for both markers discovered in the Rol selection (F1) came in clusters. These plates always harboured additional doubly transformed lines in the F2 selection. However, this could be due to a failure to find all rolling animals in the F1 selection. It is not clear how many independent events are hidden in the F2 selection.

In the examples given herein an effective distance of 120 mm and a pressure of 8 to 10 bar was used for all shots. Variation of pressure (6 to 10 bar) and distance was observed to have very little effect on the efficiency of transformation. When plates were viewed under a microscope after a shot many worms in the centre of the plate were found to be killed and the worms around this zone contained gold particles (FIG. 1) while worms in the outer zone did not. It thus seems that the velocity gradient is very steep and under the conditions of the examples used herein there is a narrow zone of transformation which may come to lie in different positions within the worm pellet depending on pressure and distance. An important factor is to place the worms in a thin and fairly dry bacterial lawn, otherwise the worms are blown away. Concerning the amount of worms used per shot, sufficient worms were used to span the shooting area but not too many worms as it becomes awkward to handle too many F1 worms for the Rol selection or an even larger number of F2 worms for pha-1 selection.

Variation in the efficiency of the transformation procedure is observed to occur even in repeat experiments in which no adaptation is made to the protocol i.e. using identical amounts of DNA, the same settings on the gun and identical culture conditions for the nematodes. Closer observation shows that bombardment experiments in which the worms remained in the centre of the plate after bombardment resulted in higher transformation efficiencies than experiments in which the worms were blown away from the centre of the plate. Moreover, worms that are blown away by the high pressure of the gun did not survive the bombardment procedure.

The reproducibility and, to a lesser extent, the efficiency of the ballistic transformation procedure can be improved by using very dry agar plates, agar plates containing a high concentration of agar and agar plates which have not been seeded with *E. coli*. Furthermore, immobilization of the worms on the agar plate will also result in enhanced efficiency and reproducibility of the ballistic transformation.

In summary, it has been demonstrated that *C. elegans* can be transformed by ballistic bombardment. At present the method is about as efficient as the microinjection procedure which, however, depends much more on the training and skill of the person carrying out the procedure and on much more expensive equipment. Unlike microinjection, where dehydration of the worms helps to relieve the internal pressure of the nematode and thus avoids bursting when they are penetrated by the needle, no ballistic transformation was achieved with dehydrated worms.

Shot Experiment: 1
*C. elegans*-strain: pha-1 (e2123)
Marker-DNA:
    1. Selection with pRF4 (rol-6); individual F1 at 15° C.
    2. Selection with pBX (pha-1); together F2/3 at 25° C.
Test-DNA:
Addition of nucleic acid:
Status: concluded

TABLE 1 results of shot experiment 1

| current shot no. | 1. selection (rol-6) | | | | Test-DNA | | | | 2. selection (pha-1) | | | |
|---|---|---|---|---|---|---|---|---|---|---|---|---|
| | 1 | 2 | 3 | 4 | 1 | 2 | 3 | 4 | 1 | 2 | 3 | 4 |
| 1 | 1 | | | | | | | | | | | |
| 2 | | | | | | | | | | | | |
| 3 | | 1 | | | | | | | X | | | |
| 4 | | | | | | | | | | | | |
| 5 | 4 | | | | | | | | $X_{Rol}$ | X | $X_{Rol}$ | $X_{Rol}$ |
| 6 | 2 | | | | | | | | | | | |
| 7 | 2 | 2 | | | | | | | $X_{Rol}$ | $X_{Rol}$ | | |
| 8 | 2 pha | | | | | | | | $X_{Rol}$ | | | |
| 9 | | | | | | | | | | $X_{Rol}$ | | |
| 10 | 2 | | | | | | | | | | | |
| 11 | 2 | | | | | | | | | | | |
| 12 | 1 | | | | | | | | $X_{Rol}$ | | | |
| 13 | 1 | 1 | | | | | | | | | | |
| 14 | | 12 | | | | | | | | | | |
| 15 | | | | | | | | | | | | |
| 16 | | 7 pha | | | | | | | | $X_{Rol}$ | | |
| 17 | 1 | 10 pha | | | | | | | $X_{Rol}$ | $X_{Rol}$ | $X_{Rol}$ | |
| 18 | | | 1 | | | | | | | | | |

Shot Experiment: 4
*C. elegans*-strain: pha-1 (e2123)
Marker-DNA:
    1. Selection with pRF4 (rol-6); individual F1 at 15° C.
    2. Selection with pBX (pha-1); together F2/3 at 25° C.
Test-DNA: pH1-FM6.9 (sud-1) after crossing with vab-9 sud-1
Addition of nucleic acid:
Status: concluded

TABLE 2 results of shot experiment 4

| current shot no. | 1. selection (rol-6) | | | | Test-DNA (sud-1) | | | | 2. selection (pha-1) | | | |
|---|---|---|---|---|---|---|---|---|---|---|---|---|
| | 1 | 2 | 3 | 4 | 1 | 2 | 3 | 4 | 1 | 2 | 3 | 4 |
| 1 | | | | | | | | | | | | |
| 2 | | | | | | | | | | X | | |
| 3 | 1 | 1 | | | | | | | | | | |
| 4 | 1 | 4 | 2 | 3 | | | | | | X | | |
| 5 | 1 | | 1 | | | | | | | | | |
| 6 | | | | | | | | | | | | |
| 7 | | 4 | 1 | 2 pha | | | | | $X_{Rol/pha}$ | | | |

TABLE 2-continued

| | results of shot experiment 4 | | | | | | | | | | | |
|---|---|---|---|---|---|---|---|---|---|---|---|---|
| current | 1. selection (rol-6) | | | | Test-DNA (sud-1) | | | | 2. selection (pha-1) | | | |
| shot no. | 1 | 2 | 3 | 4 | 1 | 2 | 3 | 4 | 1 | 2 | 3 | 4 |
| 8 | | | | | | | | | | | | |
| 9 | 2 | | 2 | 3 | | | | | | | | |
| 10 | 1 | 1 | 3 | 1 pha | | | X$_{Rol/pha}$ | | | | | |
| 11 | | | | | | | | | | | | |
| 12 | | | | | | | | | | | | |
| 13 | | | | | | | | | | | | |
| 14 | | | | | | | | | | | | |
| 15 | | | | | | | | | | | | |
| 16 | 1 | | 1 | | | | | | | | | |
| 17 | 2 | 2 | | 1 | | | | | | | | |
| 18 | | | | | | | | | | | | |
| 19 | 2 | | 2 | | | | | | | | | |
| 20 | | | | | | | | | | | | |

Shot Experiment: 6
*C. elegans*-strain: pha-1 (e2123)
Marker-DNA:
  1. Selection with pRF4 (rol-6); individual F1 at 15° C.
  2. Selection with pBX (pha-1); together F2/3 at 25° C.

Test-DNA: pH1-FM6.9 (sud-1) after crossing with vab-9 sud-1

Addition of nucleic acid:
Status: concluded

TABLE 3

| | results of shot experiment 6 | | | | | | | | | | | |
|---|---|---|---|---|---|---|---|---|---|---|---|---|
| current | 1. selection (rol-6) | | | | Test-DNA (sud-1) | | | | 2. selection (pha-1) | | | |
| shot no. | 1 | 2 | 3 | 4 | 1 | 2 | 3 | 4 | 1 | 2 | 3 | 4 |
| 1 | 2 | | | | | | | | | | | |
| 2 | | | | | | | | | X | | | |
| 3 | | 2 | | | | | | | | | | |
| 4 | | | | | | | | | | | | |
| 5 | 2 | | | | | | | | | | | X |
| 6 | | 2 | | 3 | | | | | | | | |
| 7 | | 2 | | | | | | | | | | X$_{Rol}$ |
| 8 | | 3 | 2 | | | | | | | | | |
| 9 | | | | | | | | | | | | |
| 10 | | 1 | | | | | | | | | | |
| 11 | 4 | 2 | | | | | | | | | | |
| 12 | | | | | | | | | | | | |
| 13 | | 2 | | 2 | | | | | | | | |
| 14 | | | | | | | | | | | | |
| 15 | | | | 4 | | | | | | | | |
| 16 | 2 | 2 | | 4 pha | | X$_{Rol/pha}$ | | | X | | | X$_{Rol}$ |
| 17 | | | | | | | | | | | | |
| 18 | 1 | | 2 | | | | | | | | | |
| 19 | | | | | | | | | | | | |
| 20 | | | | | | | | | | | | X$_{Rol}$ |
| 21 | | | | | | | | | | | | |
| 22 | | | | | | | | | | | | |
| 23 | 2 pha | | 3 | | X$_{Rol/pha}$ | | | | X$_{Rol}$ | | | |
| 24 | | 3 pha | | | | X$_{Rol/pha}$ | | | | X$_{Rol}$ | | |
| 25 | | | | | | | | | | | | |
| 26 | | | | | | | | | | | | |
| 27 | | | | | | | | | | | | |
| 28 | | | | | | | | | | | | |
| 29 | | | | | | | | | | | | |
| 30 | | | | 4 | | | | | | | | |

Shot Experiment: 7
*C. elegans*-strain: pha-1 (e2123)
Marker-DNA:
  1. Selection with pRF4 (rol-6); individual F1 at 15° C.
  2. Selection with pBX (pha-1); together F2/3 at 25° C.
Test-DNA: pH1-FM6.9 (sud-1) after crossing with vab-9 sud-1
Addition of nucleic acid:
Status: concluded Shot Experiment: 8
*C. elegans*-strain: pha-1 (e2123)
Marker-DNA:
  1. Selection with pRF4 (rol-6); individual F1 at 15° C.
  2. Selection with pBX (pha-1); together F2/3 at 25° C.
DNA: pH1-FM6.9 (sud-1) after crossing with vab-9 sud-1
Addition of nucleic acid:
Status: concluded

TABLE 4 results of shot experiment 7

| shot no. | 1. selection (rol-6) 1 | 2 | 3 | 4 | Test-DNA (sud-1) 1 | 2 | 3 | 4 | 2. selection (pha-1) 1 | 2 | 3 | 4 |
|---|---|---|---|---|---|---|---|---|---|---|---|---|
| 1 | | | | | | | | | $X_{Rol}$ | | | |
| 2 | | | | | | | | | | | | |
| 3 | | | | | | | | | $X_{Rol}$ | | | |
| 4 | | | | | | | | | | | | $X_{Rol}$ |
| 5 | | 3 | 2 | | | | | | | X | | |
| 6 | | | | | | | | | | | | |
| 7 | 3 pha | | | 4 | $X_{Rol/pha}$ | | | | X | | | |
| 8 | 2 | 4 pha | | | | $X_{Rol/pha}$ | | | | X | | |
| 9 | | | 2 pha | 3 pha | | | $X_{Rol/pha}$ | $X_{Rol/pha}$ | | | X | X |
| 10 | | | | 3 | | | | | X | | | |
| 11 | 2 pha | | | | $X_{Rol/pha}$ | | | | $X_{Rol}$ | | | |
| 12 | 2 | 4 | | | | | | | | | | |
| 13 | | | | | | | | | $X_{Rol}$ | | | |
| 14 | | | | | | | | | | | | |
| 15 | | | 3 pha | | | | $X_{Rol/pha}$ | | | | $X_{Rol}$ | X |
| 16 | | | | | | | | | $X_{Rol}$ | | | |
| 17 | 2 pha | | | | $X_{Rol/pha}$ | | | | X | | | |
| 18 | | | | | | | | | $X_{Rol}$ | | | |
| 19 | | | | | | | | | | | | |
| 20 | 2 | | 3 | | | | | | $X_{Rol}$ | | | |

TABLE 5 results of shot experiment 8

| shot no. | 1. selection (rol-6) 1 | 2 | 3 | 4 | Test-DNA (sud-1) 1 | 2 | 3 | 4 | 2. selection (pha-1) 1 | 2 | 3 | 4 |
|---|---|---|---|---|---|---|---|---|---|---|---|---|
| 1 | | | | | | | | | | | | |
| 2 | | | | | | | | | | | | |
| 3 | | 2 | | | | | | | | | | |
| 4 | | 2 pha | | 2 pha | | | | | $X_{Rol/pha}$ | | | |
| 5 | | 1 pha | | 5 pha | | | | | $X_{Rol/pha}$ | | | |
| 6 | | | 2 pha | | | | | | | | | |
| 7 | | | | | | | | | | | | |
| 8 | | | | | | | | | | | | |
| 9 | | | | | | | | | | | | |
| 10 | | | | | | | | | | | | |
| 11 | | | | 2 pha | | | | | | | | |
| 12 | | | | | | | | | | | | |
| 13 | | | | | | | | | | | | |
| 14 | | | | | | | | | | | | |
| 15 | | | | | | | | | | | | |
| 16 | | | | | | | | | | | | |
| 17 | | | | | | | | | | | | |
| 18 | | 2 pha | | | | | | | | | | |
| 19 | | | | | | | | | | | | |
| 20 | | | | | | | | | | | | |

Shot Experiment: 9
C. elegans-strain: pha-1 (e2123)
Marker-DNA:
  1. Selection with pRF4 (rol-6); individual F1 at 15° C.
  2. Selection with pBX (pha-1); together F2/3 at 25° C.
Test-DNA: pFM (ceh-13::lacZ) fluorescence in F2/3
Addition of nucleic acid:
Status: concluded Shot Experiment: 10
C. elegans-strain: pha-1 (e2123)
Marker-DNA:
  1. Selection with pRF4 (rol-6); individual F1 at 15° C.
  2. Selection with pBX (pha-1); together F2/3 at 25° C.
Test-DNA: pFM (ceh-13::lacZ) fluorescence in F2/3
Addition of nucleic acid: tRNA
Status: concluded

TABLE 6 results of shot experiment 9

| current shot no. | 1. selection (rol-6) | | | | Test-DNA (ceh-13) | | | | 2. selection (pha-1) | | | |
|---|---|---|---|---|---|---|---|---|---|---|---|---|
| | 1 | 2 | 3 | 4 | 1 | 2 | 3 | 4 | 1 | 2 | 3 | 4 |
| 1 | | | | | | | | | | | | |
| 2 | | | | | | | | | | | | |
| 3 | | | 1 pha | | | | | | | | | |
| 4 | | 2 pha | 2 pha | | | | | | | | | |
| 5 | | | | | | | | | | | | |
| 6 | | | | 2 | | | | | | | | |
| 7 | | | | | | | | | | | | |
| 8 | | | | 3 pha | | | | | $X_{Rol/pha}$ | | | |
| 9 | | | 2 pha | | | | | | | | | |
| 10 | | | | | | | | | | | | |
| 11 | | | | | | | | | | | | |
| 12 | | | | | | | | | | | | |
| 13 | | | | | | | | | | | | |
| 14 | | | | | | | | | | | | |
| 15 | | | | | | | | | | | | |
| 16 | | 2 | | | | | | | | | | |
| 17 | 1 pha | | | 3 | | | | | | | | |
| 18 | | | | | | | | | | | | |
| 19 | | 2 pha | 2 | 1 | | | | | | | | |
| 20 | | | | | | | | | | | | |

TABLE 7 results of shot experiment 10

| current shot no. | 1. selection (rol-6) | | | | Test-DNA (ceh-13) | | | | 2. selection (pha-1) | | | |
|---|---|---|---|---|---|---|---|---|---|---|---|---|
| | 1 | 2 | 3 | 4 | 1 | 2 | 3 | 4 | 1 | 2 | 3 | 4 |
| 1 | | | | | | | | | | | | |
| 2 | | | 3 pha | | | | | | $X_{Rol/pha}$ | | | |
| 3 | 2 pha | | | | | | | | | | | |
| 4 | | | 2 pha | | | | | | | | | |
| 5 | | | | | | | | | | | | |
| 6 | | | | | | | | | | | | |
| 7 | | | 3 pha | | | | | | | | | |
| 8 | | | | | | | | | | | | |
| 9 | 2 pha | | | | | | | | | | | |
| 10 | | | 1 pha | | | | | | | | | |
| 11 | | | | | | | | | | | | |
| 12 | | | | | | | | | | | | |
| 13 | | | | | | | | | | | | |
| 14 | | | | | | | | | | | | |
| 15 | | | | | 2 pha | | | | | | | |
| 16 | | | 2 pha | 3 pha | | | | | | | | |
| 17 | | | 2 pha | | | | | | | | | |
| 18 | | | | | | | | | | | | |
| 19 | 2 pha | | | | | | $X_{Rol/pha}$ | | | | | |
| 20 | 3 pha | | | | | | | | | | | |

Shot Experiment: 11  
C. elegans-strain: pha-1 (e2123)  
Marker-DNA:  
   1. Selection with pRF4 (rol-6); individual F1 at 15° C.  
   2. Selection with pBX (pha-1); together F2/3 at 25° C.  
Test-DNA: pFM (ceh-13::lacZ) fluorescence in F2/3  
Addition of nucleic acid:  
Status: interrupted!

Shot Experiment: 12  
C. elegans-strain: pha-1 (e2123)  
Marker-DNA:  
   1. Selection with pRF4 (rol-6); individual F1 at 15° C.  
   2. Selection with pBX (pha-1); together F2/3 at 25° C.  
Test-DNA: pFM (ceh-13::lacZ) fluorescence in F2/3  
Addition of nucleic acid:  
Status: interrupted!

TABLE 8 results of shot experiment 11

| current shot no. | 1. selection (rol-6) | | | | Test-DNA (ceh-13) | | | | 2. selection (pha-1) | | | |
|---|---|---|---|---|---|---|---|---|---|---|---|---|
| | 1 | 2 | 3 | 4 | 1 | 2 | 3 | 4 | 1 | 2 | 3 | 4 |
| 1 | | | | | | | | | | | | X |
| 2 | 2 | 1 | | | | | | | | | | |
| 3 | | | | | | | | | | | | |
| 4 | | | 3 | | | | | | | | X | |
| 5 | | 2 | | | | | | | | X | | |
| 6 | | 2 | 1 | | | | | | | | | |
| 7 | | | | | | | | | | | | |
| 8 | | | 1 | | | | | | | | X | |
| 9 | | 1 | 2 | | | | | | | | | |
| 10 | | | | | | | | | | | | |
| 11 | | | 1 | | | | | | | | | |
| 12 | | | | | | | | | | | | |
| 13 | | | | | | | | | | | | |
| 14 | 1 | | | | | | | | | | | |
| 15 | 3 | 1 | | | | | | | | | | |
| 16 | 2 | 3 | | | | | | | | X | | |
| 17 | | 6 | | | | | | | | X | | |
| 18 | | | | 1 | | | | | | | | X |
| 19 | | | | | X | | | | | | | |
| 20 | | | | | | | | | | | | |

TABLE 9 results of shot experiment 12

| current shot no. | 1. selection (rol-6) | | | | Test-DNA (ceh-13) | | | | 2. selection (pha-1) | | | |
|---|---|---|---|---|---|---|---|---|---|---|---|---|
| | 1 | 2 | 3 | 4 | 1 | 2 | 3 | 4 | 1 | 2 | 3 | 4 |
| 1 | | 2 | | | | | | | | | | |
| 2 | | | | 2 | | | | | | | | |
| 3 | | | | | | | | | | | | |
| 4 | | | | | | | | | | | | |
| 5 | | | | | | | | | | | | |
| 6 | | | | | | | | | | | | |
| 7 | 1 | 3 | | | | | | | | | | |
| 8 | | | | | | | | | | | | |
| 9 | | | 2 | | | | | | | | | |
| 10 | | | | | | | | | | | | |
| 11 | | 2 | | | | 2 | | | | | | |
| 12 | 1 | 2 | 1 | 2 | | | | | | | | |
| 13 | | | 2 | 1 | | | | | | | | |
| 14 | | | 2 | | | | | | | | | |
| 15 | | | | | | | | | | | | |
| 16 | 2 | 2 | | | | | | | | | | |
| 17 | 3 | | | | | | | | | | | |
| 18 | | 2 | | | | | | | | | | |
| 19 | | | | | | | | | | | | |
| 20 | 1 | | 3 | | | | | | | | | |

Explanation Key to Tables

| current | 1. selection (rol-6) | | | | Test-DNA (xxx-xx) | | | | 2. selection (pha-1) | | | |
|---|---|---|---|---|---|---|---|---|---|---|---|---|
| shot no. | 1 | 2 | 3 | 4 | 1 | 2 | 3 | 4 | 1 | 2 | 3 | 4 |
| 1 | | | | | | | | | | | | |
| 2 | 2 | | | | | | | | | | | |
| 3 | | 3 | | 2 | | X$_{Rol/pha}$ | | | | | | |
| 4 | | | | | | | | | | | | |
| 5 | | | | | | | | | | X | | |
| 6 | | 2 pha | | | | | | | | | | |
| 7 | | | | | | | | | | | | |
| 8 | | 3 | | 4 pha | | | | | | X | X$_{Rol}$ | |
| 9 | | | | | | | | | | | | |
| 10 | | | | | | | | | | | | |

First (Rol-6) and second (pha-1) selections were carried out on the same secondary plates 1–4, however, both selection procedures are independent of one another.

| ☐ | selection path not evaluated or carried out |
|---|---|
| Shot No. 2 | On one of four secondary plates 2 F1 animals were identified with phenotype Rol-6 and isolated; they produced no Rol-6 offspring (F2–F4); <u>transient transformation</u> |
| Shot No. 3 | On two of four secondary plates 3 and 2 F1 animals were identified with phenotype Rol-6 and isolated; they produced Rol-6 offspring in case 3/2 and no Rol-6 offspring in case 3/4 (F2–F4); <u>stable and transient transformation</u> |
| Shot No. 6 | On one of four secondary plates 2 F1 animals were identified with phenotype Rol-6 and isolated; they produced no Rol-6 offspring (F2–F4) but exhibited phenotypical rescue of pha-1; <u>transient transformation re Rol-6 but stable transformation re pha-1</u> |
| Shot No. 5 | On one of four secondary plates, under selection conditions (= 25° C.), phenotypical rescue of pha-1 was observed in F2 and F3 animals; stable after several generations; <u>stable transformation</u> |
| Shot No. 8 | On two of four secondary plates 4 and 3 F1 animals were identified with phenotype Rol-6 and isolated; in case 8/2 they produced no Rol-6 offspring and in case 8/3 they produced Rol-6 offspring (F2–F4); moreover, co-transformation was also carried out re pha-1; <u>stable and transient transformation</u> On two of four secondary plates, under selection conditions (=25° C.), phenotypical rescue of pha-1 was observed in F2 and F3 animals; stable after several generations; in one case (8/3) stable co-transformation re Rol-6 was evident; <u>stable co-transformation re pha-1 and Rol-6</u> In case 8/2 transiently transformed Rol-6 offspring refer to co-transformation re pha-1; In case 8/3 stable transformation re Rol-6 could be verified over both selection paths. |
| Shot No. 3 | Stably transformed lines were investigated further regarding the co-transformation re a particular DNA-test species; in ceh-13:: gfp (pFM) by epifluorescence and in sud-1 (pH1-FM6.9) by crossing with vab-9 sud-1 (t-1237); in each case 5 Rol-6 positive animals were (pFM) by epifluorescence and in sud-1 (pH1-FM6.9) by crossing with vab-9 sud-1 (t-1237); in each case 5 Rol-6 positive animals were tested in this respect; <u>positive re DNA test</u> |

TABLE 10

| | | A | | | | | | |
|---|---|---|---|---|---|---|---|---|
| | | rol-6 selection F1 | | | | | | |
| | | shots | | indep. | stable | cotransformation | | |
| | Series | #of shots | negative | transformants | transform. | transform. | pha-1 | ceh-13::GFP | sud-1 |
| (9) | #1 | 20 | 12 | 24 | 12 | 1 | 1 | 1 | — |
| (10) | #2 | 20 | 9 | 25 | 12 | 2 | 2 | 2 | — |
| (8) | #3 | 20 | 14 | 23 | 8 | 2 | 2 | — | 2 |

TABLE 10-continued

| | Series | # of shots | shots negative | transformants | indep. transform. | stable transform. | cotransform. pha-1 | shots negative | stable transform. | cotransform. rol-6 |
|---|---|---|---|---|---|---|---|---|---|---|
| (7) | #4 | 20 | 10 | 44 | 17 | 7 | 7 | — | | 7 |

B

| | Series | # of shots | shots negative | transformants | indep. transform. | stable transform. | cotransform. pha-1 | shots negative | stable transform. | cotransform. rol-6 |
|---|---|---|---|---|---|---|---|---|---|---|
| | | | | rol-6 selection F1 | | | | pha-1 selection F2 | | |
| (7) | #4 | 20 | 10 | 44 | 16 | 7 | 7 | 4 | 17 | 9 |
| (6) | #5 | 30 | 12 | 56 | 23 | 3 | 3 | 22 | 8 | 5 |
| (1) | #6 | 18 | 4 | 52 | 21 | 3 | 3 | 6 | 15 | 13 |

Table 10 shows the results of transformation of *C. elegans* by particle bombardment. Pha-1 (e2123) hermaphrodites were used in all experiments. (A) animals were transformed with the plasmids pRF4 (rol-6) and pBX (pha-1). In addition, a third DNA was tested for its co-expression. A ceh-13::GFP construct was properly expressed in transgenic embryos as revealed by fluorescence microscopy (see Wittman et al., as described above). A maternal effect mutation of sud-1 (t1237) was also complemented by the co-transformed plasmid pH1-FM6.9 (described above) in the transgenes as revealed by test crosses. Currently about half the shots do not reveal any transformants. Transformation events are clustered (Table Y) probably due to single transformed hermaphrodites. (transformants) indicates the number of all Rol animals; (indep transformants) indicates Rol animals derived from different slices of the original plate shot at and thus animals which arose independently. See also (B) for more data about the rol-6 selection. (B) in this series of experiments transformants were also selected in the F2 with the pha-1 system. Co-transformed stable lines were isolated in about half of the shots. Because of the clustering observed with rol-6 it is not clear if these lines represent single events. Therefore lines should be clones out to establish isogenic lines.

TABLE 11

| Shot No. | rol-6 selection | | | | pha-1 selection | | | |
|---|---|---|---|---|---|---|---|---|
| | 1 | 2 | 3 | 4 | 1 | 2 | 3 | 4 |
| 1 | 1 R | | | | | | | |
| 2 | | | | | | | | |
| 3 | | 1 R | | | | P | | |
| 4 | | | | | | | | |
| 5 | 4 R | | | | P R | P | P R | P R |
| 6 | 2 R | | | | | | | |
| 7 | 2 R | 2 R | | | P R | P R | | |
| 8 | 2 R P | | | | P R | | | |
| 9 | | | | | | | P R | |
| 10 | 2 R | | | | | | | |
| 11 | 2 R | | | | | | | |
| 12 | 1 R | | | | P R | | | |
| 13 | 1 R | 1 R | | | | | | |
| 14 | | 12 R | | | | | | |
| 15 | | | | | | | | |
| 16 | | 7 R P | | | | P R | | |
| 17 | 1 R | 10 R P | | | P R | P R | P R | |
| 18 | | | 1 R | | | | | |

Table 11 shows analysis of the shots of series #6. All experiments were evaluated as shown here. The worms corresponding to a shot are distributed to 4 plates for selection of transgenic animals as described in part (C) of Example 2. (R) rolling transformant. (P) pha-1 transformant. Normal font indicates transient expression of the rol marker. The numbers of animals found in the Rol selection is indicated. The animals from a slice were reared together to test stable expression of the rol marker. These lines were then tested for co-transformation with pha-1. Bold font indicates stable expression of the markers.

EXAMPLE 3

Alternative Technique for Ballistic Transformation

The worms are prepared for ballistic transformation according to part (A) of Example 2. A drop of a high concentration solution of nucleic acid (1 mg/ml or more) is placed onto the worm pillow and allowed to dry. The worms are then bombarded with microprojectiles which have not been coated with any nucleic acid according to the protocol given in part (B) of Example 2 and transformants are selected.

What is claimed is:

1. A method of introducing a nucleic acid into a nematode worm that is *C. elegans,* which method comprises:

bombarding the worm with a plurality of microprojectiles under conditions to permit the plurality of the microprojectiles to penetrate the worm, wherein the worm is coated with the nucleic acid and wherein the worm is not dehydrated.

2. A method as claimed in claim 1 wherein the nematode worm carries a conditional lethal mutant gene and the nucleic acid comprises a plasmid containing a wild-type equivalent of the conditional lethal mutant gene.

3. A method as claimed in claim 1 wherein the nucleic acid encodes a dominant phenotypic marker.

4. A method as claimed in claim 3 wherein the dominant phenotypic marker is Rol-6 or an autonomous fluorescent protein.

5. A method as claimed in claim 1 which further comprises placing the nematode worm onto a thin, dry bacterial lawn prior to bombarding the worm with the plurality of microprojectiles.

6. A method as claimed in claim 1 which further comprises placing the nematode worm onto a dry polymer plate prior to bombarding the worm with the plurality of microprojectiles.

7. A method as claimed in claim 6 wherein the polymer is agar.

8. A method as claimed in claim 6, which further comprises chilling the nematode worm prior to bombarding the worm with the plurality of microprojectiles.

9. A method as claimed in claim 1, which further comprises chilling the nematode worm prior to bombarding the worm with the plurality of microprojectiles.

10. A method as claimed in claim 1 in which the nematode worm is immobilized prior to bombardment with the plurality of microprojectiles.

11. A method as claimed in claim 10, wherein the nematode worm is immobilized by placing the worm onto a dry polymer plate and chilling the plate on ice prior to bombarding.

12. A method as claimed in claim 1 wherein the microprojectiles are gold particles or activated glass particles.

13. A method as claimed in claim 1, which further comprises selecting a transformant worm.

14. A method as claimed in claim 13, wherein selecting a transformant worm comprises selecting a stable transformant worm.

15. A method as claimed in claim 13, which further comprises allowing the transformant worm to produce larvae.

16. A method as claimed in claim 15, which further comprises allowing the larvae to develop into a progeny nematode worm.

17. A method for selecting a nematode worm that is *C. elegans* and that heritably transmits a nucleic acid to a subsequent generation, which method comprises:

(a) bombarding said worm with a plurality of microprojectiles under conditions to permit the nucleic acid to be retained in the worm, wherein the worm is coated with the nucleic acid;

(b) selecting a transformant worm;

(c) allowing the transformant worm to produce larvae that develop into a progeny worm; and (d) determining whether the progeny worm comprises the nucleic acid.

* * * * *